United States Patent
Blackburn et al.

(10) Patent No.: US 12,036,001 B2
(45) Date of Patent: Jul. 16, 2024

(54) METHOD FOR OPTICALLY DETECTING TOOTH MINERALIZATION

(71) Applicant: MSTATT LLC, Cleveland, OH (US)

(72) Inventors: Brecken Blackburn, Cleveland Heights, OH (US); Matthew McPheeters, Cleveland Heights, OH (US)

(73) Assignee: MSTATT LLC, Cleveland, OH (US)

( * ) Notice: Subject to any disclaimer, the term of this patent is extended or adjusted under 35 U.S.C. 154(b) by 0 days.

(21) Appl. No.: 17/287,750

(22) PCT Filed: Nov. 14, 2019

(86) PCT No.: PCT/US2019/061365
§ 371 (c)(1),
(2) Date: Apr. 22, 2021

(87) PCT Pub. No.: WO2020/102475
PCT Pub. Date: May 22, 2020

(65) Prior Publication Data
US 2021/0401292 A1 Dec. 30, 2021

Related U.S. Application Data

(60) Provisional application No. 62/767,484, filed on Nov. 14, 2018.

(51) Int. Cl.
*A61B 5/00* (2006.01)
(52) U.S. Cl.
CPC .......... *A61B 5/0095* (2013.01); *A61B 5/4547* (2013.01)

(58) Field of Classification Search
CPC ............................ A61B 5/0095; A61B 5/4547
See application file for complete search history.

(56) References Cited

U.S. PATENT DOCUMENTS

| | | | |
|---|---|---|---|
| 3,653,373 A * | 4/1972 | Batterman | A61B 5/1111 73/579 |
| 7,796,243 B2 | 9/2010 | Choo-Smith et al. | |
| 2004/0077949 A1 | 4/2004 | Blofgett et al. | |
| 2004/0106081 A1 * | 6/2004 | Karazivan | A61B 5/4547 433/29 |
| 2007/0233056 A1 | 10/2007 | Yun | |
| 2008/0032255 A1 * | 2/2008 | Pitts | A61B 5/4547 433/32 |
| 2008/0294016 A1 * | 11/2008 | Gobeyn | A61B 5/411 600/301 |

(Continued)

FOREIGN PATENT DOCUMENTS

AU 2002245263 7/2002

OTHER PUBLICATIONS

International Search Report and Written Opinion for corresponding International Patent Application No. PCT/US2019/061365 mailed on Jan. 29, 2020.

(Continued)

*Primary Examiner* — Nicholas D Lucchesi
(74) *Attorney, Agent, or Firm* — Renner, Otto, Boisselle & Sklar, LLP

(57) ABSTRACT

An apparatus for detecting changes in dental tissue by detecting a spectral change of dental tissue by comparing Acoustic Phonon Mediated Optical Scattering (APMOS) spectroscopic data to a baseline signal.

20 Claims, 4 Drawing Sheets

(56) References Cited

U.S. PATENT DOCUMENTS

| | | | |
|---|---|---|---|
| 2013/0189641 A1* | 7/2013 | Perfect | A61B 1/247 433/29 |
| 2015/0010878 A1* | 1/2015 | Seibel | A61B 5/0071 433/215 |
| 2018/0146857 A1* | 5/2018 | González Fernández | G01J 3/44 |
| 2021/0199566 A1* | 7/2021 | Haji Reza | A61B 5/0035 |

OTHER PUBLICATIONS

Blodgett et al.; Laser Ultrasonic Techniques for Assessment of Tooth Structure; Proceedings of Spie; IEEE; U.S.; vol. 3914; Jan. 22, 2000; pp. 588-598.

Extended European Search Report issued for co-pending European Regional Phase Application No. 19885047.1.

* cited by examiner

112

METHOD FOR OPTICALLY DETECTING TOOTH MINERALIZATION

RELATED APPLICATIONS

This application claims the benefit of U.S. Application No. 62/767,484 filed on Nov. 14, 2018, that is herein incorporated by reference in its entirety.

TECHNICAL FIELD

The present disclosure relates generally to dental caries and, more particularly, to using imaging to detect dental caries.

BACKGROUND

Dental caries are present in a majority of adults both worldwide and in the United States (US) and impose a significant health and ongoing financial burden. While the prevalence of caries has decreased in the US and Europe over the past half-century, caries often still go undetected and untreated, with 27% of adults in the US (2012) and 34% of adults globally (2015) having at least one untreated caries. Treatment becomes more significant the longer that caries goes untreated, with costly and sometimes painful treatments such as fillings, crowns, or tooth extraction and dental implants potentially required. Dental health worsens with age, with 13% of adults 65-74 years and 26% of adults 75+ years being edentulous.

Current dental practice has generally used a combination of tactile and radiographic methods to detect carious lesions. Caries have been traditionally viewed as an infectious disease with a normal treatment approach of tissue removal after progression through the enamel. However, improved understanding in recent years has better characterized caries as originating in disease of the biofilm covering the teeth and in imbalance between cyclical demineralization and remineralization of the tooth surface. This improving understanding has been matched by many new strategies for arresting the progression of early and mid-stage caries through biofilm management and remineralization. Additionally, public health measures (such as fluoridated water) have led typical caries to be smaller and progress more slowly in recent decades, presenting a longer window for intervention while perversely making them more difficult to detect.

Unfortunately, there is no reliable diagnostic method currently used in the dental clinic that can detect the earliest stage caries where intervention would likely be most effective. Dental probe-based assessment, in addition to potentially damaging teeth, is only effective with progressed lesions, limiting its usefulness for this purpose. The most commonly used digital radiographic methods generally become effective only when there has been significant demineralization of the enamel. This is a critical gap for remineralization and other earlier treatments to be effective. A diagnostic method which could detect changes in the properties of the enamel at the earliest stages of net demineralization would allow treatments to be applied earlier, before significant tooth decay has occurred. This, in combination with early-stage treatments, could significantly decrease the incidence of carious lesions across the population.

SUMMARY

A method and device for detecting early stage dental caries is needed. The present disclosure provides an apparatus for detecting changes in dental tissue by detecting a spectral change of dental tissue by comparing Acoustic Phonon Mediated Optical Scattering (APMOS) spectroscopic data to a baseline signal. APMOS spectroscopy allows for early-stage dental caries detection (e.g., caused by demineralization) while still reversible.

According to one aspect, there is provided a method for detecting changes in dental tissue using circuitry and an Acoustic Phonon Mediated Optical Scattering (APMOS) spectrometer. The method comprising includes, using the APMOS spectrometer, capturing spectroscopic data from a location including dental tissue. The spectroscopic data is based on inelastic scattering of light due to interaction with acoustic phonons in the dental tissue at the location. Using the circuitry, a spectral change of the spectroscopic data is identified based on a comparison between the spectroscopic data and a baseline signal. The spectral change corresponds to a difference in speed of sound in dental tissue due to a change in density at the location compared to the baseline signal. An assessment of a state of the dental tissue at the location is determined with the circuitry based on the spectral change. The determined assessment of the state of dental tissue at the location is output.

Alternatively or additionally, the baseline signal comprises at least one of a frequency location of a feature of a waveform, a width in frequency of the feature of the waveform, or an amplitude of a particular frequency in the waveform.

Alternatively or additionally, the method also includes, prior to the identification of the spectral change: using the APMOS spectrometer, capturing baseline spectroscopic data from a particular location including dental tissue. The baseline spectroscopic data is based on inelastic scattering of light due to interaction with acoustic phonons in the dental tissue located at the particular location. Using the circuitry, the baseline signal is established based on the captured baseline spectroscopic data from the particular location.

Alternatively or additionally, the particular location and the location comprise different anatomical locations on teeth of a patient. The dental tissue of the particular location is known to have a decreased likelihood of demineralization compared to the dental tissue of the location.

Alternatively or additionally, the particular location and the location are located on a same tooth of the patient.

Alternatively or additionally, the particular location comprises multiple different locations on teeth of a patient. The baseline spectroscopic data comprises spectroscopic data captured from the multiple different locations. The baseline signal is based off of the baseline spectroscopic data captured from the multiple different locations.

Alternatively or additionally, the particular location comprises multiple different locations on multiple different teeth of a patient.

Alternatively or additionally, the spectroscopic data comprises spectroscopic data from multiple different tooth locations. For each of the multiple different tooth locations, the circuitry: (1) identifies the spectral change of the spectroscopic data at the tooth location; (2) determines the assessment of the state of dental tissue at the tooth location; and (3) outputs the determined assessment of the state of dental tissue at the tooth location.

Alternatively or additionally, the spectral change comprises differences between the baseline spectroscopic data and the spectroscopic data include at least one of: frequencies present, amplitude of particular frequencies, location of a peak, or a width of a peak.

Alternatively or additionally, the determined assessment of the state of dental tissue identified at the location includes at least one of: a presence or state of dental caries; a status or level of mineralization; or a cause of the state of dental tissue at the location caused by an acid level and/or a calcium level.

Alternatively or additionally, the method also includes (1) imaging the location using a light beam used in capturing the spectroscopic data and (2) displaying an overlay of the images of the location and a visual representation of the assessment of the state of dental tissue at the location.

Alternatively or additionally, the spectroscopic data is captured using polarized light.

The present disclosure further provides an apparatus for detecting changes in dental tissue including an apparatus for detecting changes in dental tissue comprising an Acoustic Phonon Mediated Optical Scattering (APMOS) spectrometer and circuitry. The APMOS spectrometer is configured to capture spectroscopic data from a location including dental tissue. The spectroscopic data is based on inelastic scattering of light due to interaction with acoustic phonons in the dental tissue at the location. The circuitry configured to identify a spectral change of the spectroscopic data based on a comparison between the spectroscopic data and a baseline signal. The spectral change corresponds to a difference in speed of sound in dental tissue due to a change in density at the location compared to the baseline signal. The circuitry also determines an assessment of a state of the dental tissue at the location based on the spectral change. The circuitry further outputs the determined assessment of the state of dental tissue at the location.

Alternatively or additionally, the baseline signal comprises at least one of a frequency location of a feature of a waveform, a width in frequency of the feature of the waveform, or an amplitude of a particular frequency in the waveform.

Alternatively or additionally, the APMOS spectrometer is further configured to capture baseline spectroscopic data from a particular location including dental tissue. The circuitry is further configured to establish the baseline signal based on the captured baseline spectroscopic data from the particular location.

Alternatively or additionally, the particular location and the location comprise different anatomical locations on teeth of a patient. The dental tissue of the particular location is known to have a decreased likelihood of demineralization compared to the dental tissue of the location.

Alternatively or additionally, the particular location and the location are located on a same tooth of the patient.

Alternatively or additionally, the particular location comprises multiple different locations on teeth of a patient. The baseline spectroscopic data comprises spectroscopic data captured from the multiple different locations. The baseline signal is based off of the baseline spectroscopic data captured from the multiple different locations.

Alternatively or additionally, the particular location comprises multiple different locations on multiple different teeth of a patient.

Alternatively or additionally, the spectroscopic data comprises spectroscopic data from multiple different tooth locations, For each of the multiple different tooth locations, the circuitry is further configured to: (1) identify the spectral change of the spectroscopic data at the tooth location; (2) determine the assessment of the state of dental tissue at the tooth location; and (3) output the determined assessment of the state of dental tissue at the tooth location.

Alternatively or additionally, the spectral change comprises differences between the baseline spectroscopic data and the spectroscopic data include at least one of: frequencies present, amplitude of particular frequencies, location of a peak, or a width of a peak.

Alternatively or additionally, the determined assessment of the state of dental tissue identified at the location includes at least one of: a presence or state of dental caries; a status or level of mineralization; or a cause of the state of dental tissue at the location comprising an acid level and/or a calcium level.

Alternatively or additionally, the apparatus further comprises an image sensor configured to image the location using a light beam used in capturing the spectroscopic. The circuitry is configured to display an overlay of the images of the location and a visual representation of the assessment of the state of dental tissue at the location.

Alternatively or additionally, the APMOS is configured to capture the spectroscopic data using polarized light.

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

DETAILED DESCRIPTION

Figure 1:
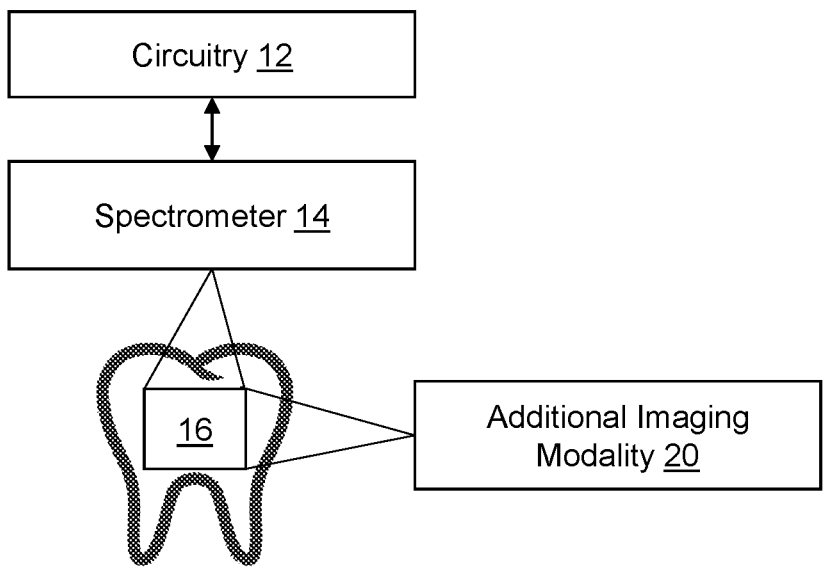
FIG. 1 is a block diagram of an exemplary apparatus for detecting changes in dental tissue.

The present invention is now described in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

The present invention provides an apparatus for detecting changes in dental tissue using circuitry and Acoustic Phonon Mediated Optical Scattering (APMOS) spectrometer. APMOS spectroscopic data is captured for dental tissue at a location of interest. The captured spectroscopic data is compared to a baseline signal (also referred to as a baseline) to detect a spectral change. The state of the dental tissue at the location of interest is assessed based on the spectral change.

Figure 2:
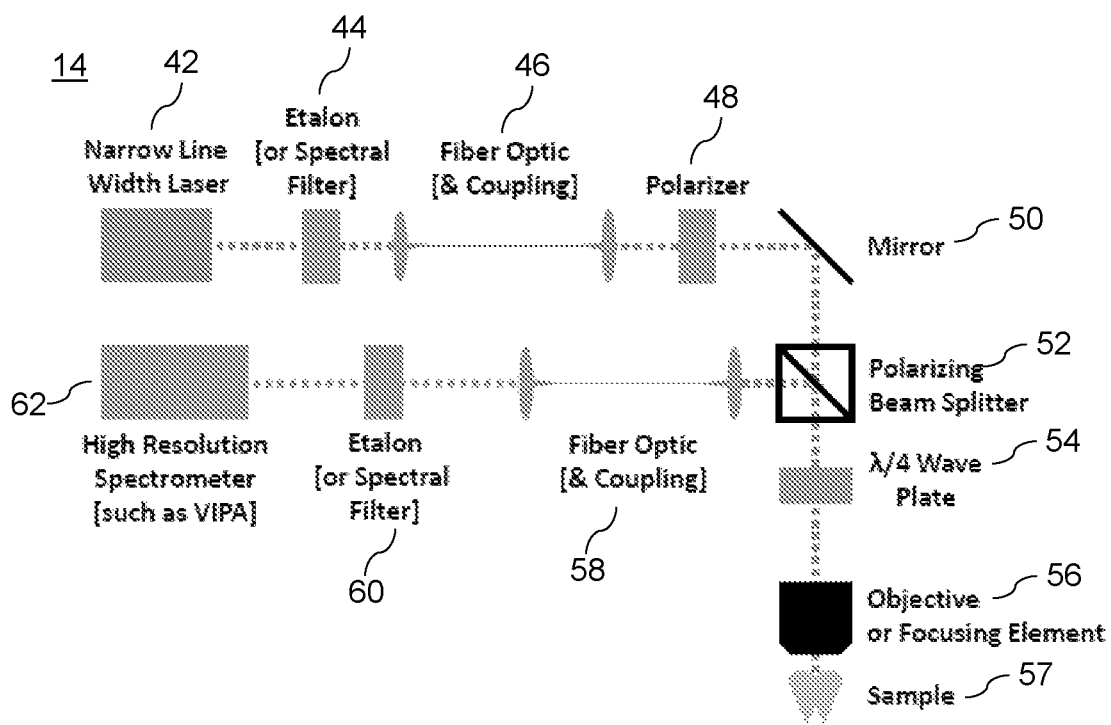
FIG. 2 is a block diagram of the optical setup of an exemplary apparatus of FIG. 1.

Turning to FIGS. 1 and 2, an exemplary apparatus for detecting changes in dental tissue 10 according to the invention includes circuitry 12 and an Acoustic Phonon Mediated Optical Scattering (APMOS) spectrometer 14. The APMOS spectrometer 14 captures spectroscopic data from a location including dental tissue. The captured spectroscopic data is based on inelastic scattering of light due to interaction with acoustic phonons in the dental tissue at the location. The circuitry 12 receives the captured spectroscopic data and identifies a spectral change of the spectroscopic data based on a comparison between the spectroscopic data and a baseline. Based on the spectral change, the circuitry 12 determines and outputs an assessment of a state of the dental tissue at the location.

The APMOS spectrometer 14 uses APMOS spectroscopy to measure properties of dental tissue. APMOS spectroscopy is a spectroscopic method for measuring spectral shifts due to inelastic scattering specifically mediated by acoustic phonons.

In any solid object, random thermodynamic fluctuations will create small pressure waves which propagate throughout the material. These pressure waves are referred to as phonons. Though small and weak, these phonons trade energy with photons through spontaneous inelastic scattering (inelastic scattering, by definition, means scattering where the photon, upon interaction with the sample, has exchanged energy with the sample, resulting in either a higher- or lower-energy scattered photon), creating a frequency-shifting effect similar to the more commonly-known Doppler shift. The spectral change corresponds to a difference in speed of sound in dental tissue due to a change in density at the location compared to the baseline.

Figure 3:
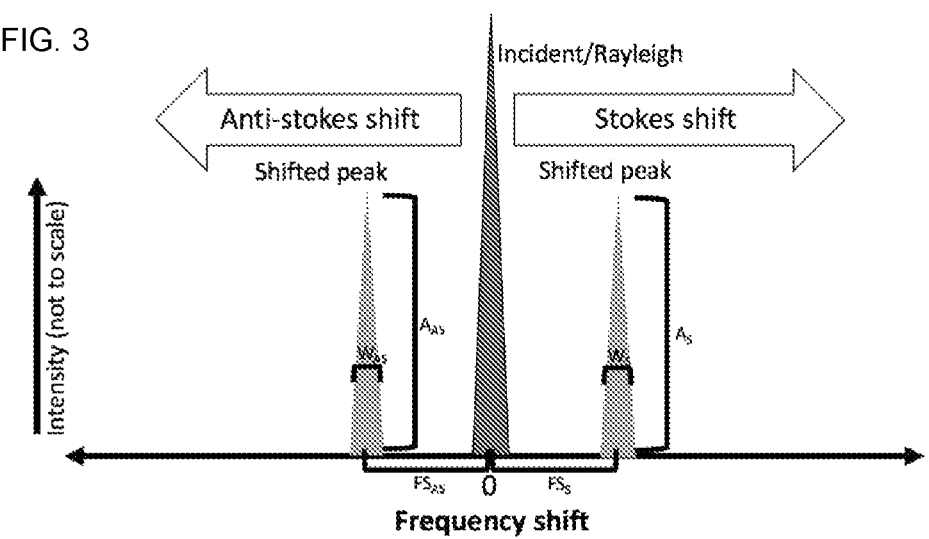
FIG. 3 is a plot of intensity vs frequency for an exemplary spectral change having two peaks.
Figure 4:
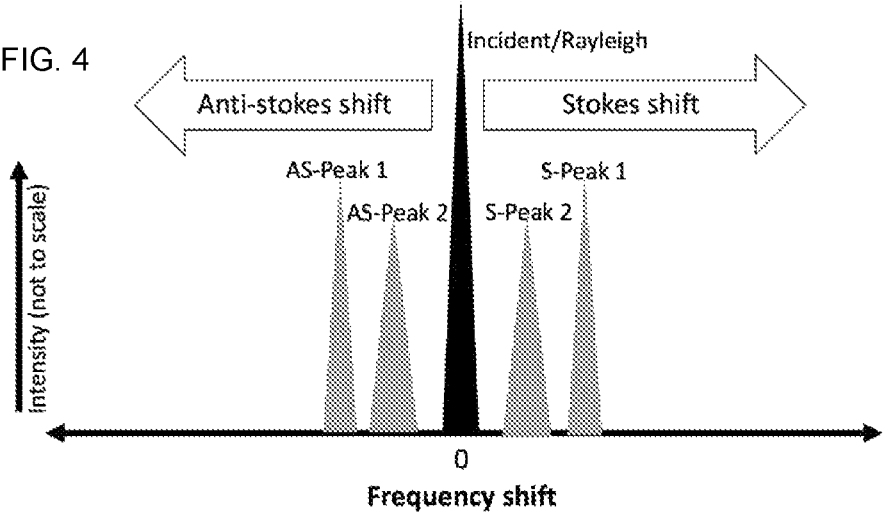
FIG. 4 is a plot of intensity vs frequency for an exemplary spectral change including four peaks.

Turning to FIGS. 3 and 4, in APMOS spectroscopy, if the incident light source is narrow bandwidth (i.e., emits a narrow frequency band of electromagnetic radiation), the shift in frequency between the incident electromagnetic radiation and the electromagnetic radiation received from the dental tissue may be measured using a high precision spectrometer 14. Such shifts may be referred to as Brillouin shifts. When compared to the Raman scattering (which has spectral shifts on the order of 1 THz), the spectral shifts produced by Brillouin inelastic scattering are much smaller (e.g., approximately 5-50 GHz).

The APMOS spectrometer 14 may utilize any suitable wavelength (e.g., visible light, infrared (IR) light, etc.) for capturing spectroscopic data from dental tissues. For example, the APMOS spectrometer 14 may utilize primarily light having a wavelength of 532 nm.

Compared to other methods of detecting dental caries, APMOS spectroscopy has the advantage of using electromagnetic radiation that is non-ionizing, avoiding the collateral health risks compared to X-Ray or CT. Similarly, unlike ultrasound, APMOS spectroscopy does not require physical contact with the enamel. Direct contact may be problematic due to the varied and intricate geometry of teeth.

As an additional advantage, APMOS imaging systems are inexpensive compared to other imaging modalities, such as MRI.

With continued reference to FIG. 2, an exemplary APMOS spectrometer 14 is shown. The APMOS spectrometer 14 includes a light source 42 (e.g., a narrow line width laser) configured to emit electromagnetic radiation as described above. The electromagnetic radiation emitted by the light source 42 is received by an etalon (or spectral filter) 44. The etalon 44 is an optical device used as a narrow band filter. The electromagnetic radiation leaving the etalon 44 is optionally received by a fiber optic 46 before reaching a polarizer 48.

A trajectory of the polarized electromagnetic radiation is optionally redirected by a mirror 50. The polarized electromagnetic radiation next passes through a polarizing beam splitter 52 that allows electromagnetic radiation having a particular polarization to pass through the beam splitter 52 and interact with a quarter wave plate 54. The rotated polarized electromagnetic radiation leaving the quarter wave plate 54 is then focused onto the sample 57 (i.e., dental tissue) using an objective 56.

The electromagnetic radiation interacts with the sample 57 and a portion of the electromagnetic radiation is received by the objective 56. The electromagnetic radiation received by the objective 54 then passes back through the quarter wave plate 54 and interacts with the polarizing beam splitter 52. A portion of the electromagnetic radiation is directed by the polarizing beam splitter 52 towards an etalon 60. The electromagnetic radiation may optionally travel from the polarizing beam splitter 52 to the etalon 60 via a fiber optic 58.

The filtered electromagnetic radiation leaving the etalon 60 is then detected using a spectrometer (e.g., a VIPA spectrometer) 62. The spectrometer 62 is configured to measure the frequencies present in the incident electromagnetic radiation along with an amplitude of the different present frequencies.

In the first stage of development, dental caries are characterized by mild abrasion and erosion by acid. This change in chemical composition due to demineralization of the dental tissues results in a change in the mechanical properties of the dental tissues, which results in a change in the speed of sound in the dental tissue and, correspondingly, a change in the characteristic phonon energies in the dental tissue (i.e., the pressure waves created by random thermodynamic fluctuations in the dental tissue described above). This change in the speed of phonons in the dental tissue causes a change in the trade of energy between the phonons and photons (i.e., Brillouin scattering), creating a frequency-shifting effect that differs between healthy dental tissues and dental tissues that have been demineralized or remineralized.

As described above, the spectral change of the spectroscopy data for the dental tissue at the location is determined based on a comparison between the captured spectroscopy data and the baseline signal. The baseline signal may comprise at least one of a: one or more frequency locations of a feature of a waveform, one or more widths in frequency of the feature of the waveform, or one or more amplitudes of a particular frequency in the waveform. For example, the baseline signal may comprise a frequency location of a peak value of the captured spectroscopy data. In this example, the spectral change may comprise a difference in frequency between the peak of the captured spectroscopic data and the frequency location identified in the baseline signal.

In the above example, the baseline signal may comprise a predetermined signal that is determined independent of a particular patient. Alternatively, the baseline signal may be determined using spectroscopic data captured from the patient. That is, prior to the identification of the spectral change, the APMOS spectrometer 14 may be used to capture baseline spectroscopic data from a particular location including dental tissue. Like the captured spectroscopic data, the baseline spectroscopic data is based on inelastic scattering of light due to interaction with acoustic phonons in the dental tissue located at the particular location. After capturing the baseline spectroscopic data, the circuitry 12 may establish the baseline signal based on the captured baseline spectroscopic data from the particular location.

With continued reference to FIGS. 3 and 4, the baseline spectroscopic data may have a stokes shift relative to the incident light, while the spectroscopic data for the location may have an anti-stokes shift. Alternatively, the direction of the shift may be the same for the spectroscopic data and the baseline spectroscopic data, but the amount of shift may be different.

Additionally, as shown in FIG. 4, the spectroscopic data and the baseline spectroscopic data may include more than one peak. That is, the spectroscopic data and the baseline spectroscopic data may include more than one peak as shown in FIG. 4.

The particular location (that the baseline spectroscopic data is captured from) and the location (that the spectroscopic data is captured from) may comprise different anatomical locations on teeth of a patient. For example, the dental tissue of the particular location may be known to have a decreased likelihood of demineralization compared to the dental tissue of the location. As an example, the particular location used to capture the baseline spectroscopic data may comprise an inner surface of the teeth that is less likely to have dental caries as compared to the location (e.g., located on a top surface of the molars).

The particular location and the location may be located on different types of teeth (e.g., incisor, molar, etc.) within a mouth of the same patient. Alternatively, the particular location and the location may be located on a same tooth of the patient. In this way, if both the particular location and the location are healthy (i.e., free of dental caries), then the spectroscopic data from these two locations should be very similar or the same.

As opposed to a single location, the particular location may comprises multiple different locations on teeth of a patient. In this example, the baseline spectroscopic data comprises spectroscopic data captured from the multiple different locations and the baseline signal is based off of the baseline spectroscopic data captured from the multiple different locations. For example, the particular location may comprise multiple different locations on multiple different teeth of a patient.

In one embodiment, the spectroscopic data may comprise spectroscopic data from multiple different tooth locations. For each of the multiple different tooth locations, the circuitry 12 may be configured to identify the spectral change of the spectroscopic data at the tooth location and determine the assessment of the state of dental tissue at the tooth location. The circuitry 12 may also output the determined assessment of the state of dental tissue at the tooth location.

The spectral change may comprise differences between the baseline spectroscopic data and the spectroscopic data including at least one of: frequencies present, amplitude of particular frequencies, location of a peak, or a width of a peak. As will be understood by one of ordinary skill in the art, the spectral change may comprise any difference between the spectroscopic data and the baseline signal that is related to a presence of dental caries.

The assessment determined by the circuitry 12 of the state of dental tissue identified at the location may include at least one of: a presence or state of dental caries; a status or level of mineralization; or a cause of the state of dental tissue at the location comprising an acid level and/or a calcium level.

The assessment of the dental tissues may not be limited to the presence and/or severity of dental caries. For example, the assessment may also provide a measure of tooth mineralization. This measure of mineralization could be used as an indicator of general health status, such as osteoporosis, diet (including acid or calcium content of diet), or other behavioral health such as bulimia which may manifest in the teeth. This measure of tooth mineralization could also be used to assess the dynamic status of dental caries (progression) or the response of the enamel to remineralization treatments. Such a tool may be used as feedback to assess needed further dental care.

Because changes to the physical structure of the dental tissues can be detected using APOMOS spectroscopy, it is possible to discriminate between caries/demineralization and other abnormalities which appear as suspicious lesion, such as surface staining, upon visible inspection or by other surveying techniques like radiography or fluorescence imaging.

Additional imaging modalities 20 may be used in conjunction with APMOS spectroscopy to detect and categorize dental caries. For example, the apparatus 10 may include Raman scattering or quantitative fluorescence imaging. In this example, these often times faster but typically less precise imaging modalities may be used to scan a large region and highlight suspicious areas, while APMOS spectroscopy may be used to classify caries highlighted by these faster modalities.

As another example, the location may be imaged using a light beam used in capturing the spectroscopic data. That is, in addition to using the incident light beam to capture spectroscopic data, the incident light beam may also be used to capture, e.g., brightfield images, optical coherence tomography (OCT) images, fluorescent images, etc. The circuitry 12 may display an overlay of the images of the location and a visual representative of the assessment of the state of dental tissue at the location. For example, the visual representation may comprise a color coding of the assessment where colors ranging from green to red are used to represent an extent of changes in mineralization.

The spectroscopic data may also be captured using polarized light. Healthy enamel typically has tightly aligned crystals that strongly reflects particular polarization states of light. As dental tissues demineralize and remineralize, the crystal structure of the dental tissues changes and is less ordered and less birefringent. Consequently, using polarized light, it is possible to reject surface reflections (specular reflection) and to identify demineralized/remineralized dental tissues.

Figure 5:
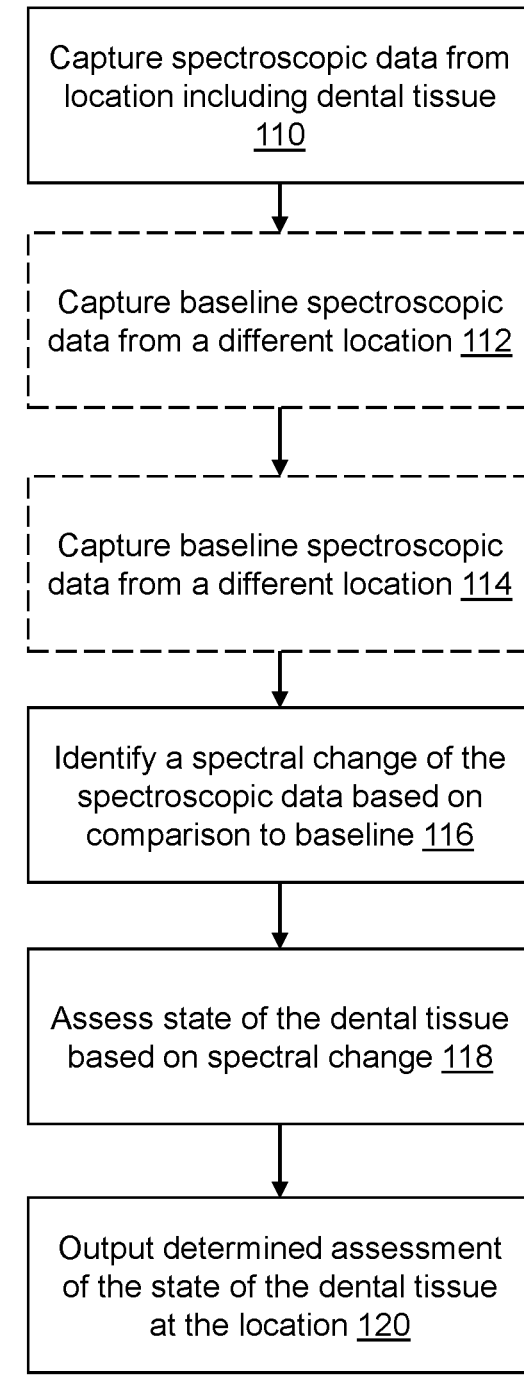
FIG. 5 is a flow diagram depicting an exemplary method for detecting changes in dental tissue using circuitry and an Acoustic Phonon Mediated Optical Scattering (APMOS) spectrometer.
Figure 6:
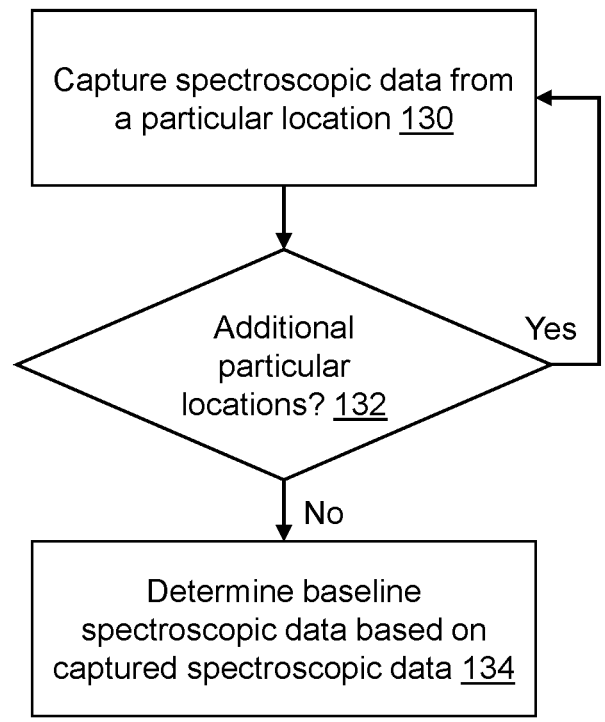
FIG. 6 is a flow diagram depicting a method for capturing baseline spectroscopic data.

Turning to FIG. 5, a method 100 for detecting changes in dental tissue using circuitry and an Acoustic Phonon Mediated Optical Scattering (APMOS) spectrometer is shown. In processing block 110, the APMOS spectrometer 14 is used to capture spectroscopic data from a location including dental tissue. In optional process block 112, the APMOS spectrometer 14 is used to capture baseline spectroscopic data from a particular location including dental tissue. In optional process block 114, the circuitry 12 is used to establish the baseline signal based on the captured baseline spectroscopic data from the particular location.

In processing block 116, the circuitry 12 is used to identify a spectral change of the spectroscopic data based on a comparison between the spectroscopic data and a baseline signal. In processing block 118, the circuitry 12 is used to determine an assessment of a state of the dental tissue at the location based on the spectral change. In process block 120, the circuitry 12 is used to output the determined assessment of the state of dental tissue at the location. For example, as described above, the assessment may be output to a display.

As will be understood by one of ordinary skill in the art, the circuitry 12 may have various implementations. For example, the circuitry 12 may include any suitable device, such as a processor (e.g., CPU), programmable circuit, integrated circuit, memory and I/O circuits, an application specific integrated circuit, microcontroller, complex programmable logic device, other programmable circuits, or the like. The circuitry 12 may also include a non-transitory computer readable medium, such as random access memory (RAM), a read-only memory (ROM), an erasable programmable read-only memory (EPROM or Flash memory), or any other suitable medium. Instructions for performing the method described below may be stored in the non-transitory computer readable medium and executed by the circuitry 12. The circuitry 12 may be communicatively coupled to the computer readable medium and network interface through a system bus, mother board, or using any other suitable structure known in the art.

It should be appreciated that many of the elements discussed in this specification may be implemented in a hardware circuit(s), a processor executing software code or instructions which are encoded within computer readable media accessible to the processor, or a combination of a hardware circuit(s) and a processor or control block of an integrated circuit executing machine readable code encoded within a computer readable media. As such, the term circuit, module, server, application, or other equivalent description of an element as used throughout this specification is, unless otherwise indicated, intended to encompass a hardware circuit (whether discrete elements or an integrated circuit block), a processor or control block executing code encoded in a computer readable media, or a combination of a hardware circuit(s) and a processor and/or control block executing such code.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A method for detecting changes in dental tissue using circuitry and an Acoustic Phonon Mediated Optical Scattering (APMOS) spectrometer, the method comprising:
   using the APMOS spectrometer, capturing spectroscopic data from a location including dental tissue, wherein the spectroscopic data is based on inelastic scattering of light due to interaction with acoustic phonons in the dental tissue at the location;
   using the circuitry, identifying a spectral change of the spectroscopic data based on a comparison between the spectroscopic data and a baseline signal, wherein the spectral change corresponds to a difference in speed of sound in dental tissue due to a change in density at the location compared to the baseline signal;
   determining with the circuitry an assessment of a state of the dental tissue at the location based on the spectral change; and
   outputting the determined assessment of the state of dental tissue at the location.

2. The method of claim 1, wherein the baseline signal comprises at least one of a frequency location of a feature of a waveform, a width in frequency of the feature of the waveform, or an amplitude of a particular frequency in the waveform.

3. The method of claim 1, further comprising, prior to the identification of the spectral change:
   using the APMOS spectrometer, capturing baseline spectroscopic data from a particular location including dental tissue, wherein the baseline spectroscopic data is based on inelastic scattering of light due to interaction with acoustic phonons in the dental tissue located at the particular location; and
   using the circuitry, establishing the baseline signal based on the captured baseline spectroscopic data from the particular location.

4. The method of claim 3, wherein:
   the particular location and the location comprise different anatomical locations on teeth of a patient; and
   the dental tissue of the particular location is known to have a decreased likelihood of demineralization compared to the dental tissue of the location.

5. The method of claim 3, wherein:
   the particular location and the location are located on a same tooth of the patient; or
   the particular location comprises multiple different locations on multiple different teeth of a patient.

6. The method of claim 3, wherein:
   the particular location comprises multiple different locations on teeth of a patient; and
   the baseline spectroscopic data comprises spectroscopic data captured from the multiple different locations; and
   the baseline signal is based off of the baseline spectroscopic data captured from the multiple different locations.

7. The method of claim 3, wherein the spectroscopic data comprises spectroscopic data from multiple different tooth locations; and
   for each of the multiple different tooth locations, the circuitry:
      identifies the spectral change of the spectroscopic data at the tooth location;
      determines the assessment of the state of dental tissue at the tooth location; and
      outputs the determined assessment of the state of dental tissue at the tooth location.

8. The method of claim 3, wherein the spectral change comprises differences between the baseline spectroscopic data and the spectroscopic data includes at least one of: frequencies present, amplitude of particular frequencies, location of a peak, or a width of a peak.

9. The method of claim 1, wherein:
the determined assessment of the state of dental tissue identified at the location includes at least one of:
a presence or state of dental caries;
a status or level of mineralization; or
a cause of the state of dental tissue at the location comprising an acid level and/or a calcium level.

10. The method of claim 1, further comprising:
imaging the location using a light beam used in capturing the spectroscopic data; and
displaying an overlay of images of the location and a visual representative of the assessment of the state of dental tissue at the location.

11. An apparatus for detecting changes in dental tissue comprising:
an Acoustic Phonon Mediated Optical Scattering (APMOS) spectrometer configured to capture spectroscopic data from a location including dental tissue, wherein the spectroscopic data is based on inelastic scattering of light due to interaction with acoustic phonons in the dental tissue at the location;
circuitry configured to:
identify a spectral change of the spectroscopic data based on a comparison between the spectroscopic data and a baseline signal, wherein the spectral change corresponds to a difference in speed of sound in dental tissue due to a change in density at the location compared to the baseline signal;
determine an assessment of a state of the dental tissue at the location based on the spectral change; and
output the determined assessment of the state of dental tissue at the location.

12. The apparatus of claim 11, wherein the baseline signal comprises at least one of a frequency location of a feature of a waveform, a width in frequency of the feature of the waveform, or an amplitude of a particular frequency in the waveform.

13. The apparatus of claim 12, wherein:
the APMOS spectrometer is further configured to capture baseline spectroscopic data from a particular location including dental tissue; and
the circuitry is further configured to establish the baseline signal based on the captured baseline spectroscopic data from the particular location.

14. The apparatus of claim 13, wherein:
the particular location and the location comprise different anatomical locations on teeth of a patient; and
the dental tissue of the particular location is known to have a decreased likelihood of demineralization compared to the dental tissue of the location.

15. The apparatus of claim 13, wherein:
the particular location and the location are located on a same tooth of the patient; or
the particular location comprises multiple different locations on multiple different teeth of a patient.

16. The apparatus of claim 13, wherein:
the particular location comprises multiple different locations on teeth of a patient; and
the baseline spectroscopic data comprises spectroscopic data captured from the multiple different locations; and
the baseline signal is based off of the baseline spectroscopic data captured from the multiple different locations.

17. The apparatus of claim 13, wherein the spectroscopic data comprises spectroscopic data from multiple different tooth locations; and
for each of the multiple different tooth locations, the circuitry is further configured to:
identify the spectral change of the spectroscopic data at the tooth location;
determine the assessment of the state of dental tissue at the tooth location; and
output the determined assessment of the state of dental tissue at the tooth location.

18. The apparatus of claim 13, wherein the spectral change comprises differences between the baseline spectroscopic data and the spectroscopic data includes at least one of: frequencies present, amplitude of particular frequencies, location of a peak, or a width of a peak.

19. The apparatus of claim 11, wherein:
the determined assessment of the state of dental tissue identified at the location includes at least one of:
a presence or state of dental caries;
a status or level of mineralization; or
a cause of the state of dental tissue at the location comprising an acid level and/or a calcium level.

20. The apparatus of claim 11:
further comprising an image sensor configured to image the location using a light beam used in capturing the spectroscopic data; and
wherein the circuitry is configured to display an overlay of images of the location and a visual representative of the assessment of the state of dental tissue at the location.

* * * * *